United States Patent
Carnahan et al.

(10) Patent No.: US 9,791,348 B2
(45) Date of Patent: Oct. 17, 2017

(54) SENSOR FOR WEAR MEASUREMENT, METHOD FOR MAKING SAME, AND METHOD FOR OPERATING SAME

(71) Applicant: NanoLab, Inc., Waltham, MA (US)

(72) Inventors: David L. Carnahan, Needham, MA (US); Iosif Izrailit, Newton, MA (US)

(*) Notice: Subject to any disclaimer, the term of this patent is extended or adjusted under 35 U.S.C. 154(b) by 107 days.

(21) Appl. No.: 14/529,879

(22) Filed: Oct. 31, 2014

(65) Prior Publication Data
US 2015/0049970 A1    Feb. 19, 2015

Related U.S. Application Data

(63) Continuation-in-part of application No. 14/054,447, filed on Oct. 15, 2013.

(60) Provisional application No. 61/713,735, filed on Oct. 15, 2012, provisional application No. 61/898,128, filed on Oct. 31, 2013.

(51) Int. Cl.
| | | |
|---|---|---|
| *G01M 13/04* | (2006.01) | |
| *G01N 27/22* | (2006.01) | |
| *B23P 11/00* | (2006.01) | |
| *H05K 3/30* | (2006.01) | |
| *F16C 17/24* | (2006.01) | |
| *F16C 17/02* | (2006.01) | |
| *F16C 23/04* | (2006.01) | |
| *G01N 3/56* | (2006.01) | |

(52) U.S. Cl.
CPC .......... *G01M 13/04* (2013.01); *B23P 11/005* (2013.01); *F16C 17/246* (2013.01); *G01N 27/22* (2013.01); *H05K 3/306* (2013.01); *F16C 17/02* (2013.01); *F16C 23/043* (2013.01); *G01N 3/56* (2013.01); *Y10T 29/49117* (2015.01); *Y10T 29/49139* (2015.01); *Y10T 29/49908* (2015.01)

(58) Field of Classification Search
None
See application file for complete search history.

(56) References Cited

U.S. PATENT DOCUMENTS

| | | | |
|---|---|---|---|
| 3,950,599 A | 4/1976 | Board, Jr. | |
| 4,006,051 A | 2/1977 | Board, Jr. | |
| 4,122,388 A | 10/1978 | Bernasconi et al. | |
| 6,324,899 B1 * | 12/2001 | Discenzo | F16C 19/52 340/631 |
| 7,166,354 B2 | 1/2007 | Tsunashima et al. | |
| 7,270,890 B2 | 9/2007 | Sabol et al. | |
| 7,354,877 B2 | 4/2008 | Rosenberger et al. | |
| 7,551,288 B1 | 6/2009 | Discenzo | |
| 2005/0109090 A1 * | 5/2005 | Pfeffer | F16D 66/02 73/121 |
| 2008/0199247 A1 * | 8/2008 | Spratte | F16C 11/0647 403/27 |
| 2009/0219040 A1 | 9/2009 | Shinde et al. | |
| 2010/0308980 A1 | 12/2010 | Gosset et al. | |
| 2011/0075382 A1 * | 3/2011 | Mackey | G06F 3/044 361/749 |
| 2012/0106095 A1 * | 5/2012 | Daniel | H05K 1/0283 361/746 |
| 2014/0103942 A1 | 4/2014 | Izrailit et al. | |

\* cited by examiner

*Primary Examiner* — Paul West
*Assistant Examiner* — Mark A Shabman
(74) *Attorney, Agent, or Firm* — Pandiscio & Pandiscio

(57) ABSTRACT

A spherical bearing comprising:
a race;
a ball;
a wear lining; and
a capacitive sensor positioned within or behind the wear lining to gauge wear of said wear lining.

11 Claims, 17 Drawing Sheets

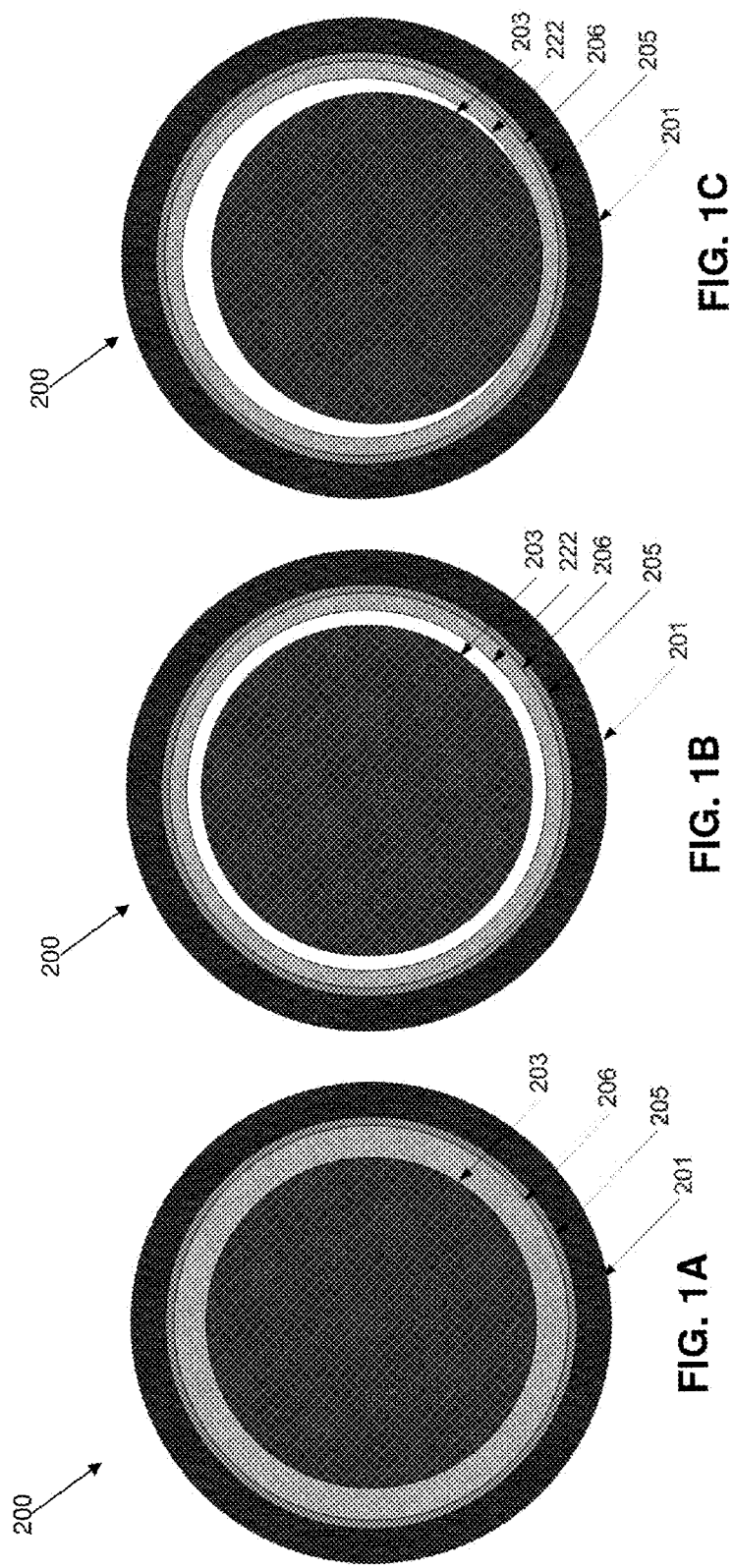

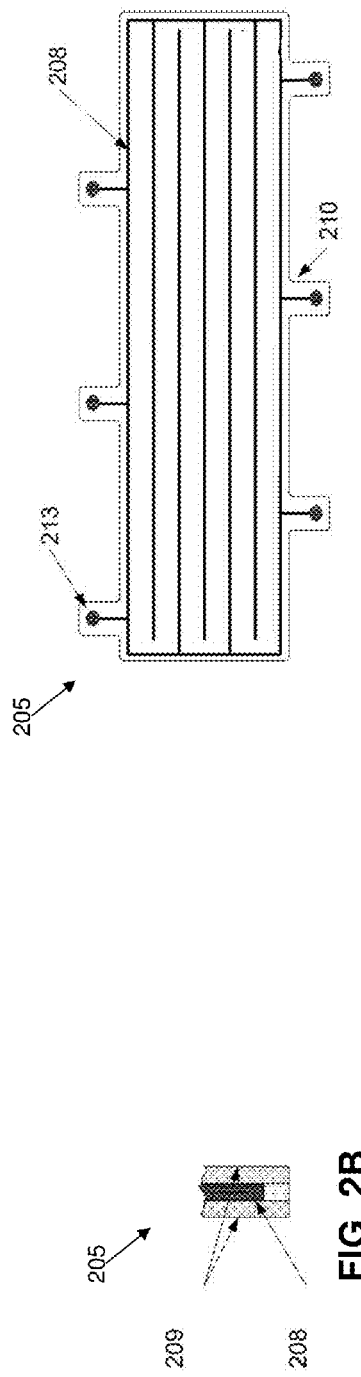
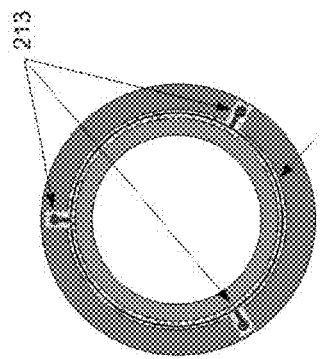
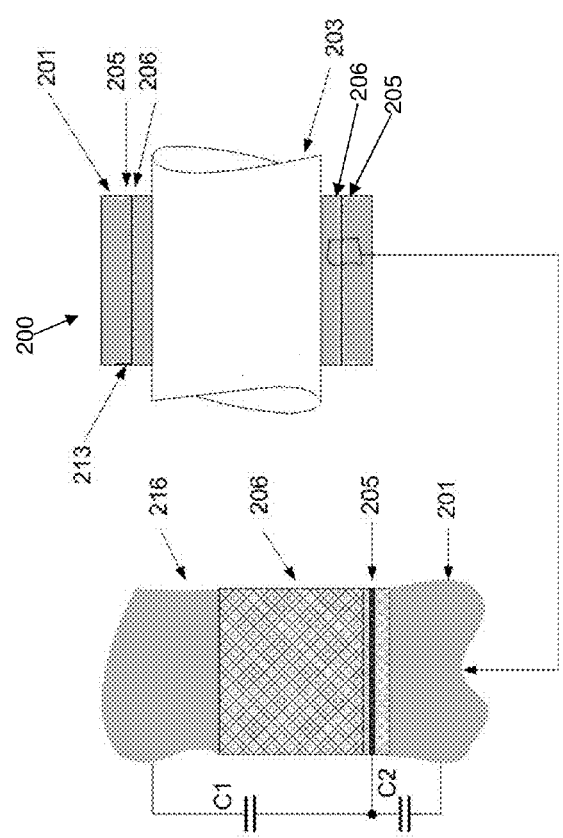
FIG. 2C
FIG. 2D
FIG. 2B
FIG. 2A

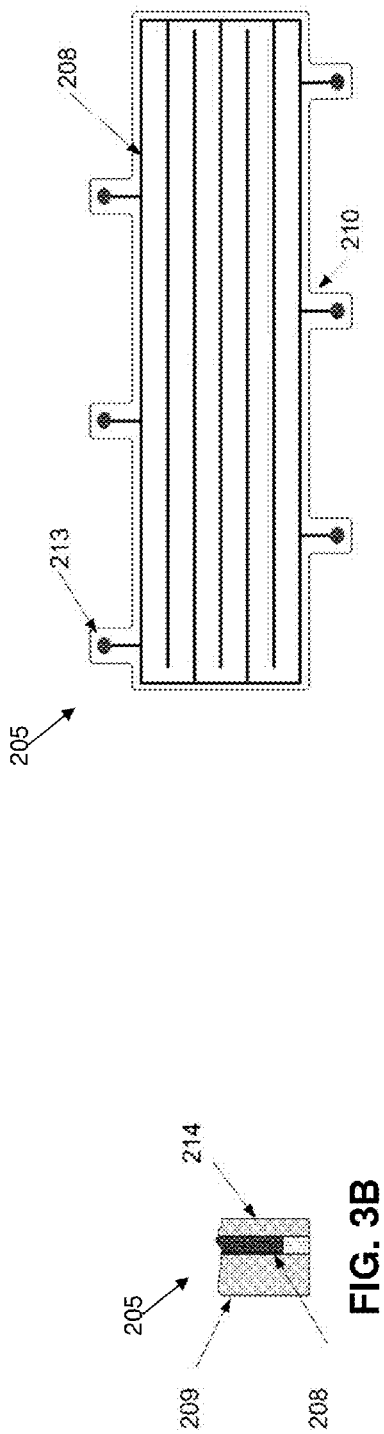
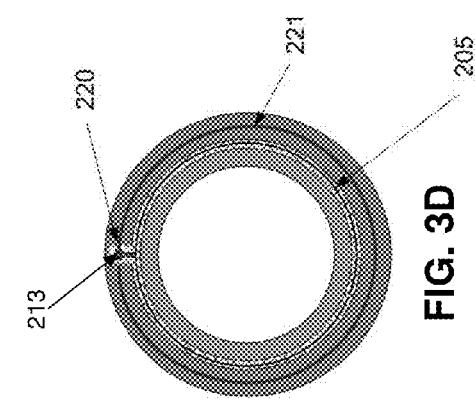
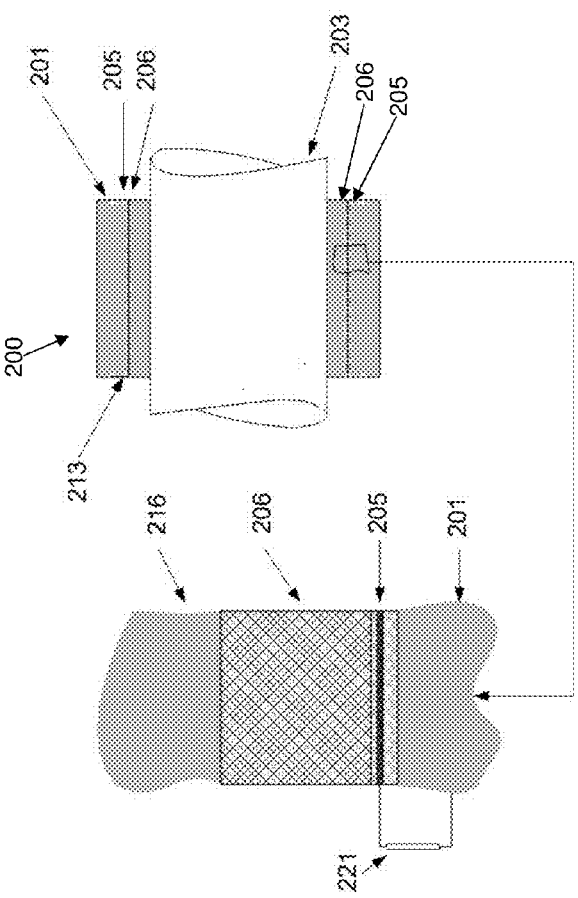
FIG. 3C
FIG. 3D
FIG. 3B
FIG. 3A

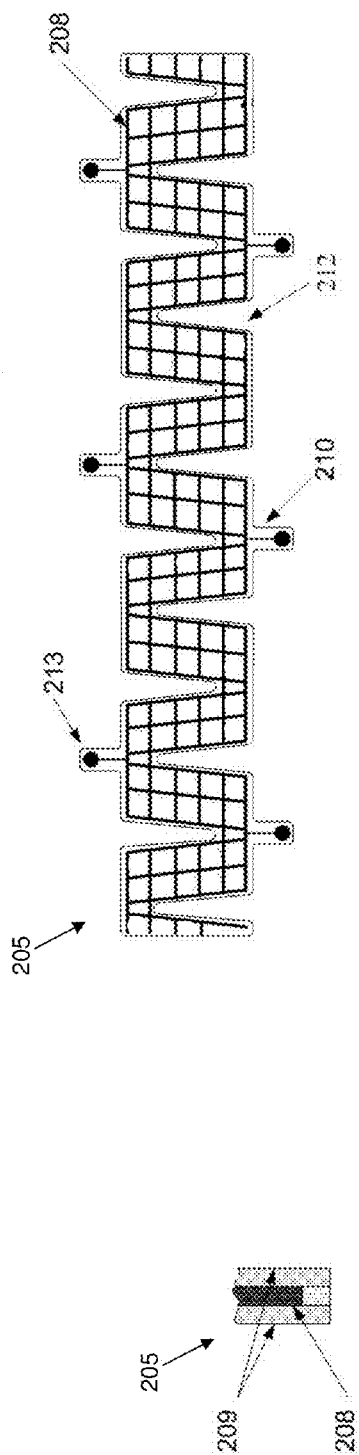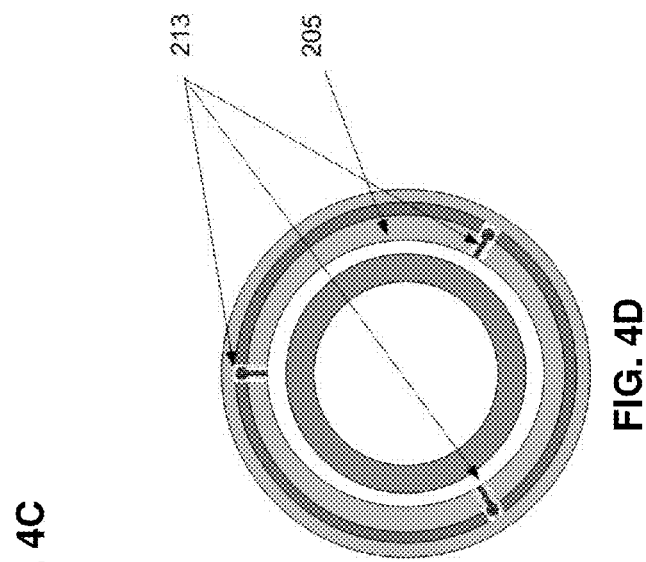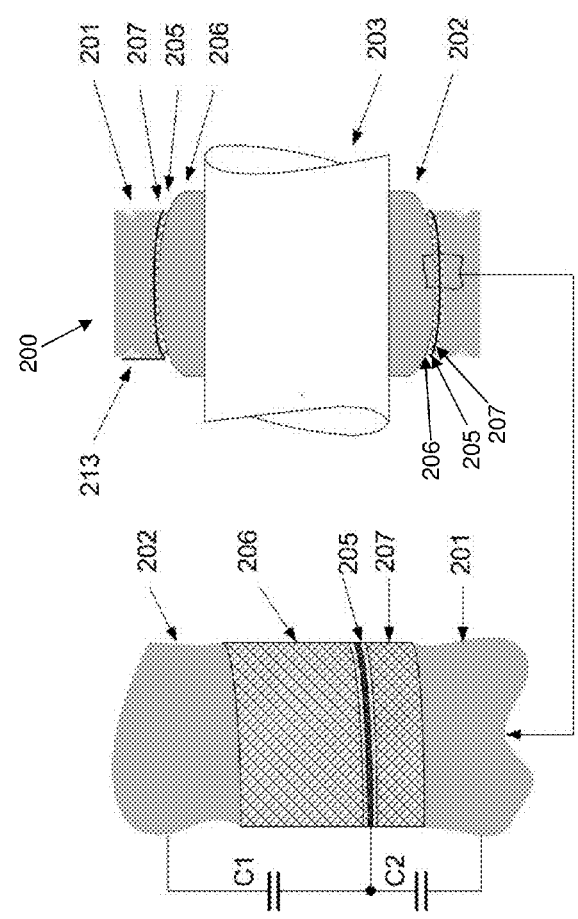

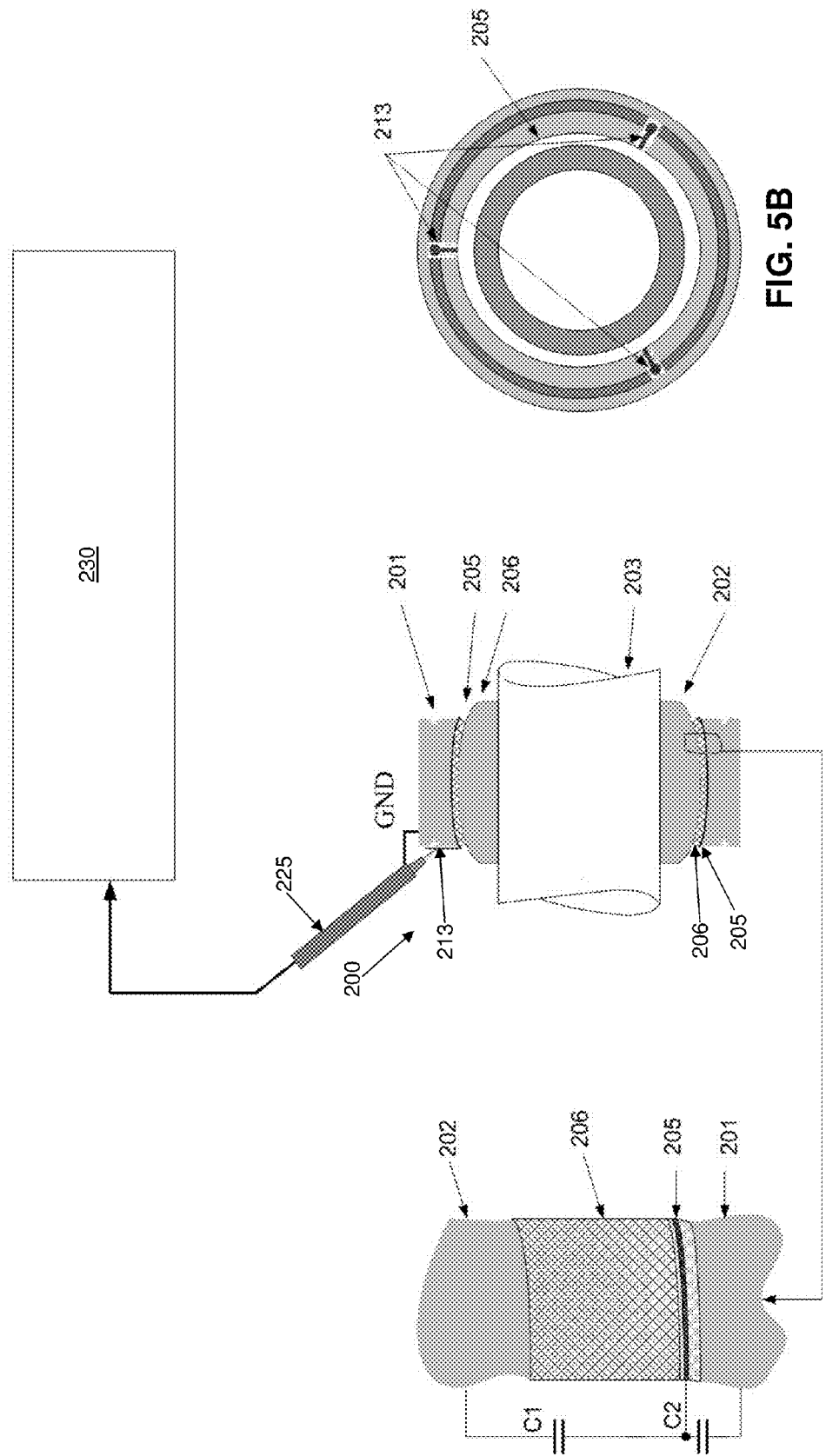

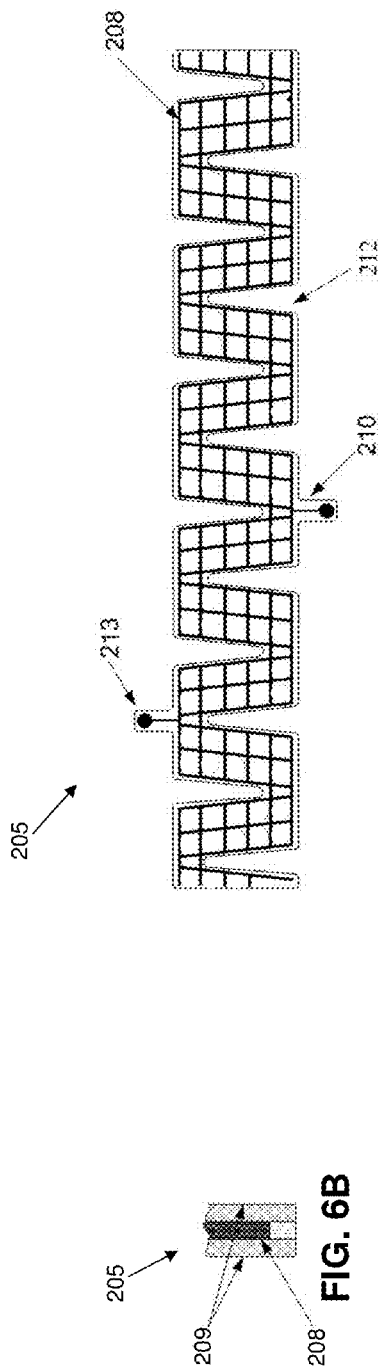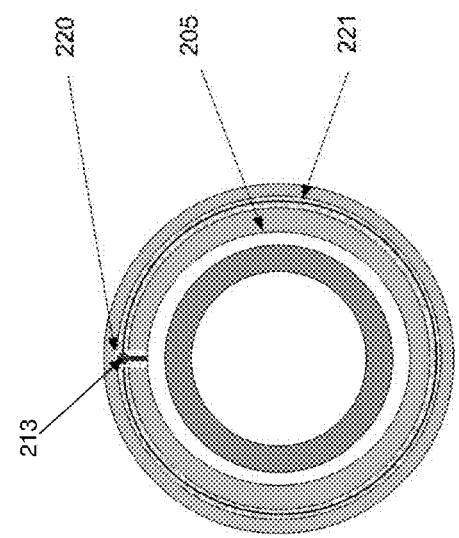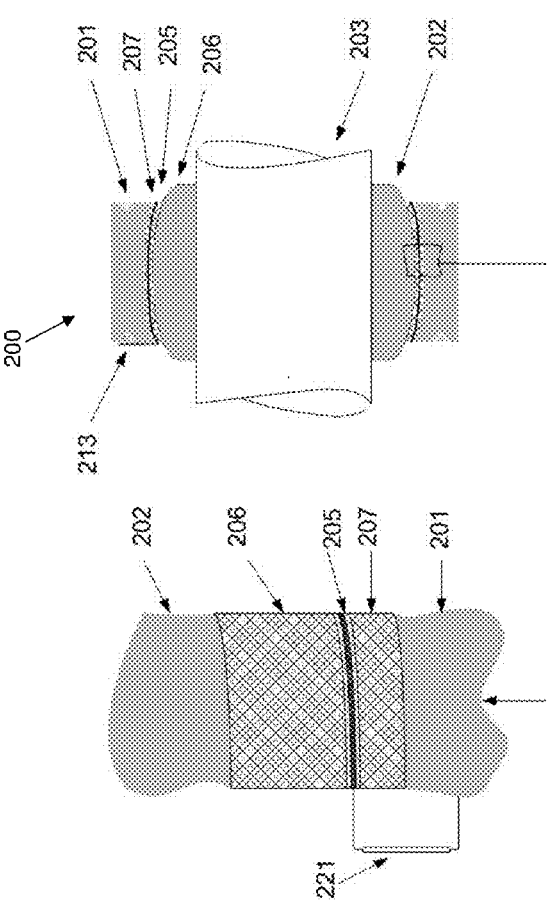

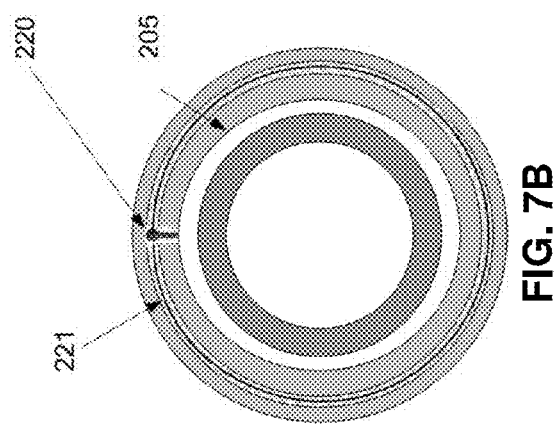
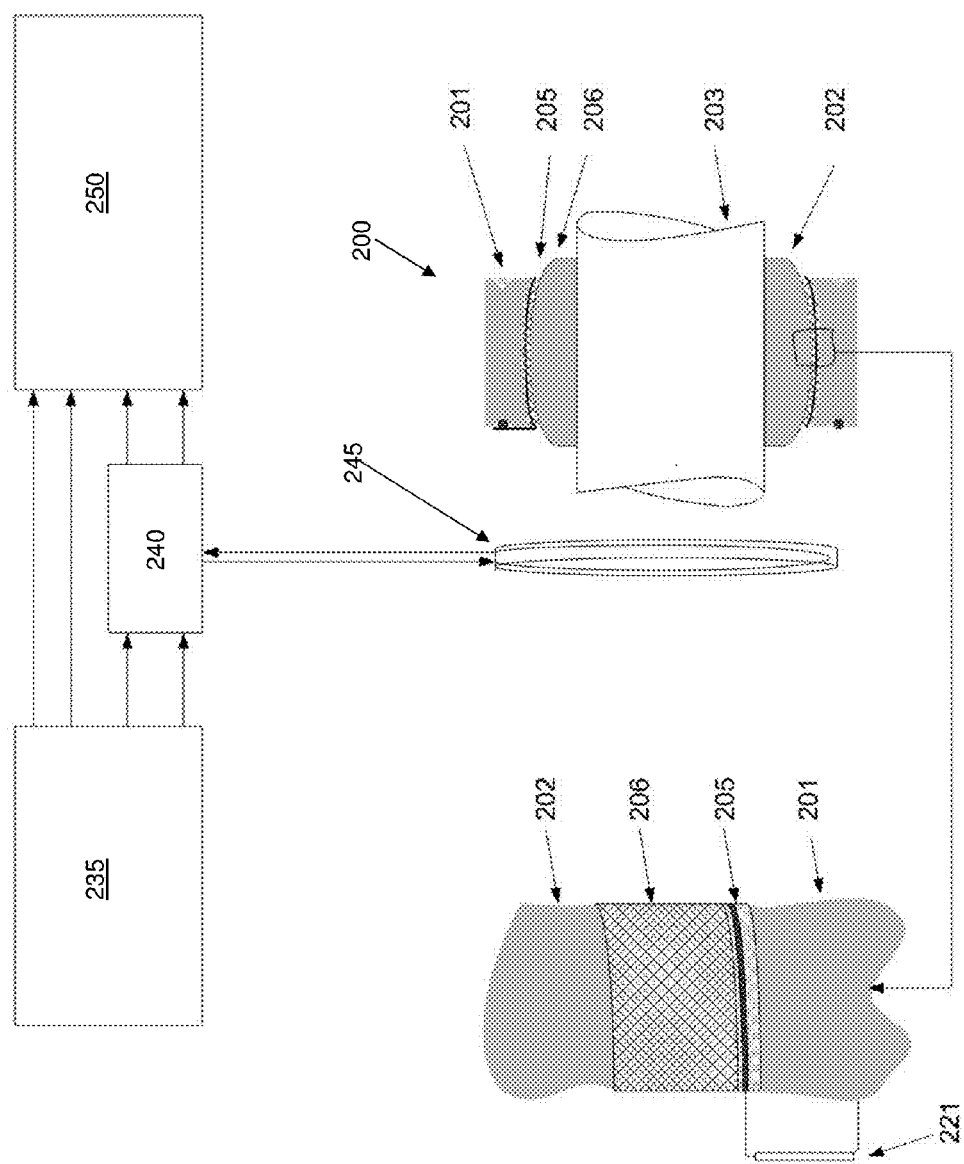
FIG. 7B
FIG. 7A

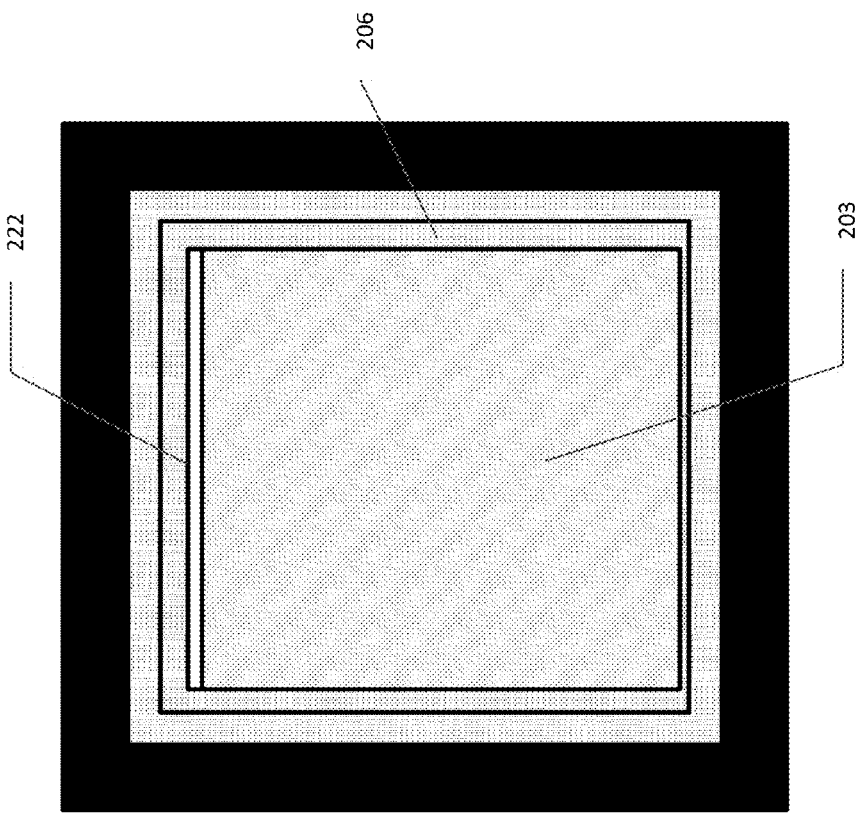
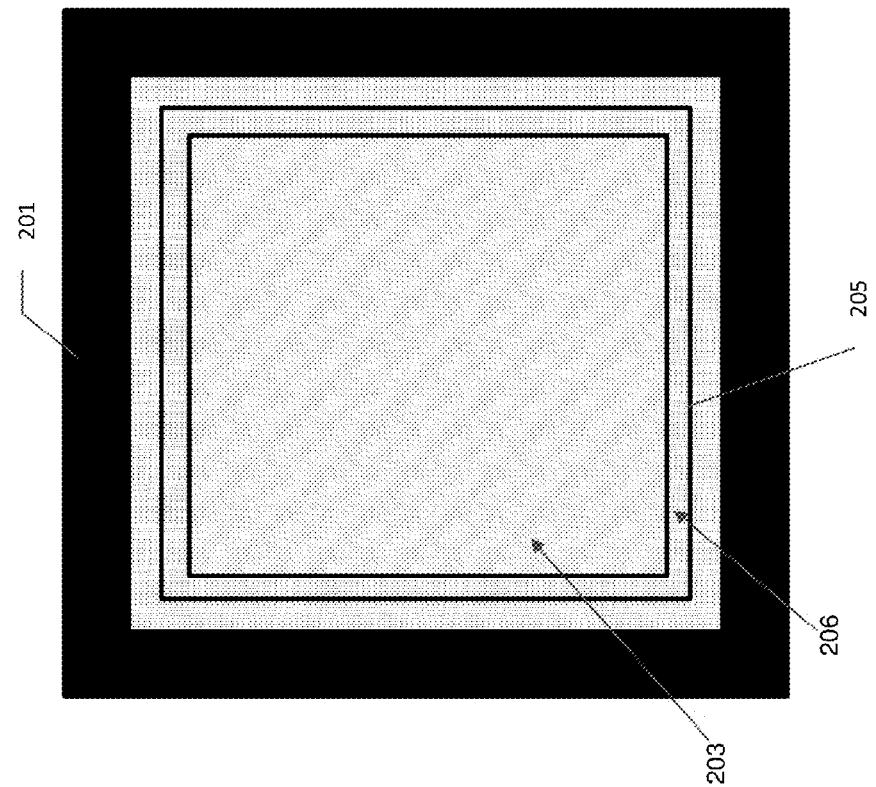
FIG. 8A
FIG. 8B

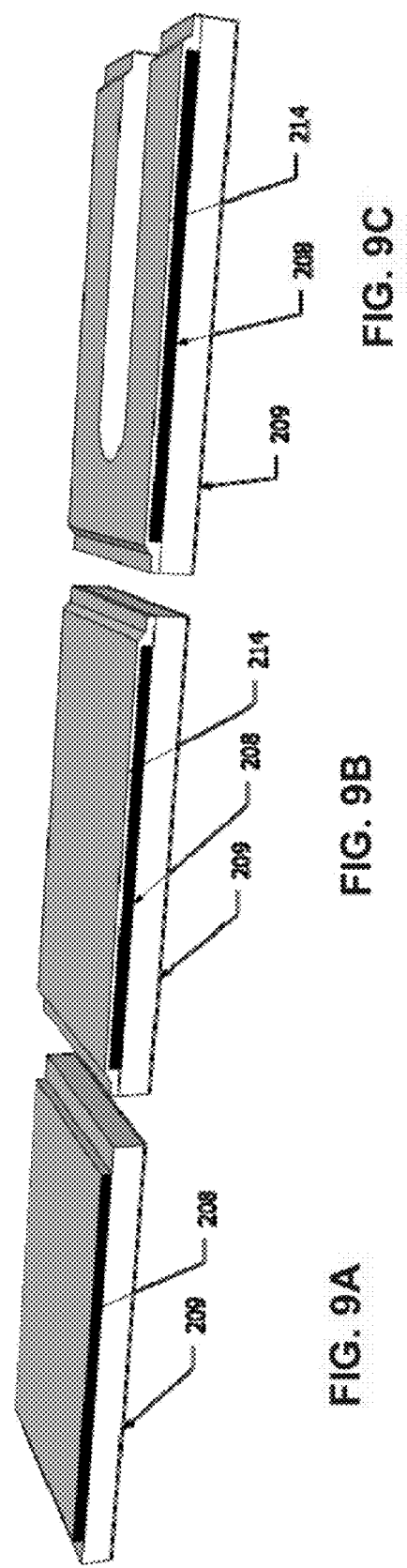

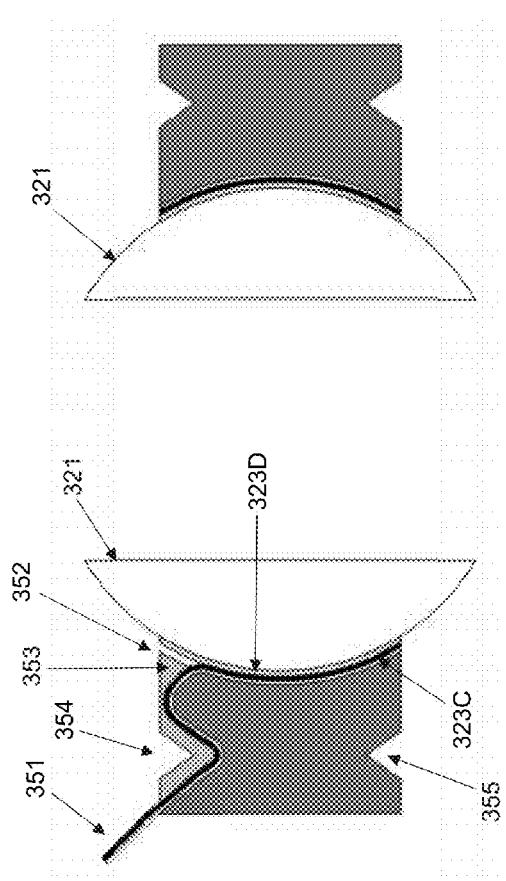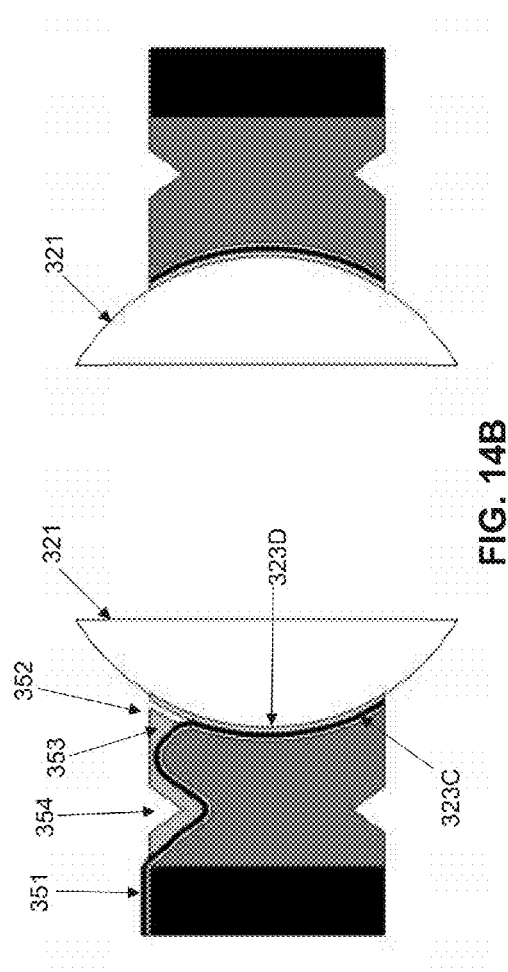

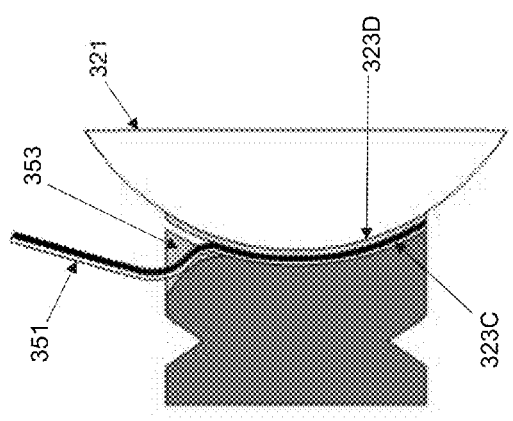
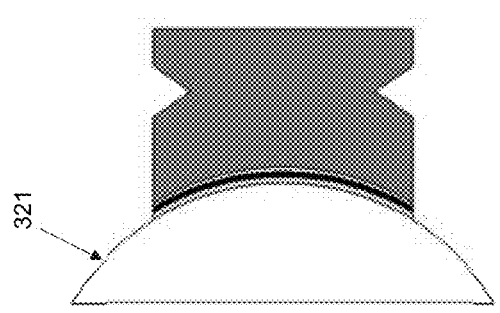
FIG. 15A
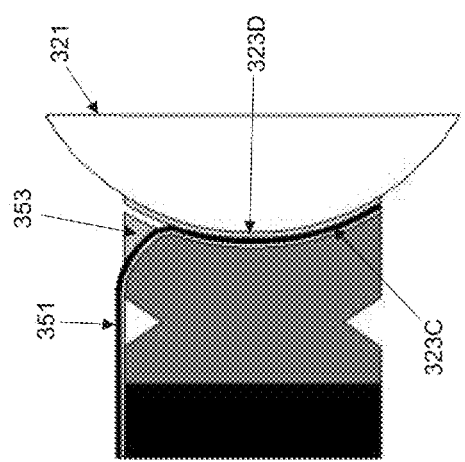
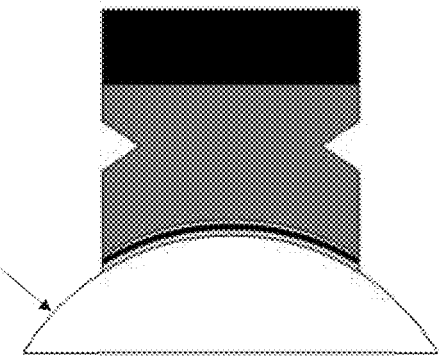
FIG. 15B

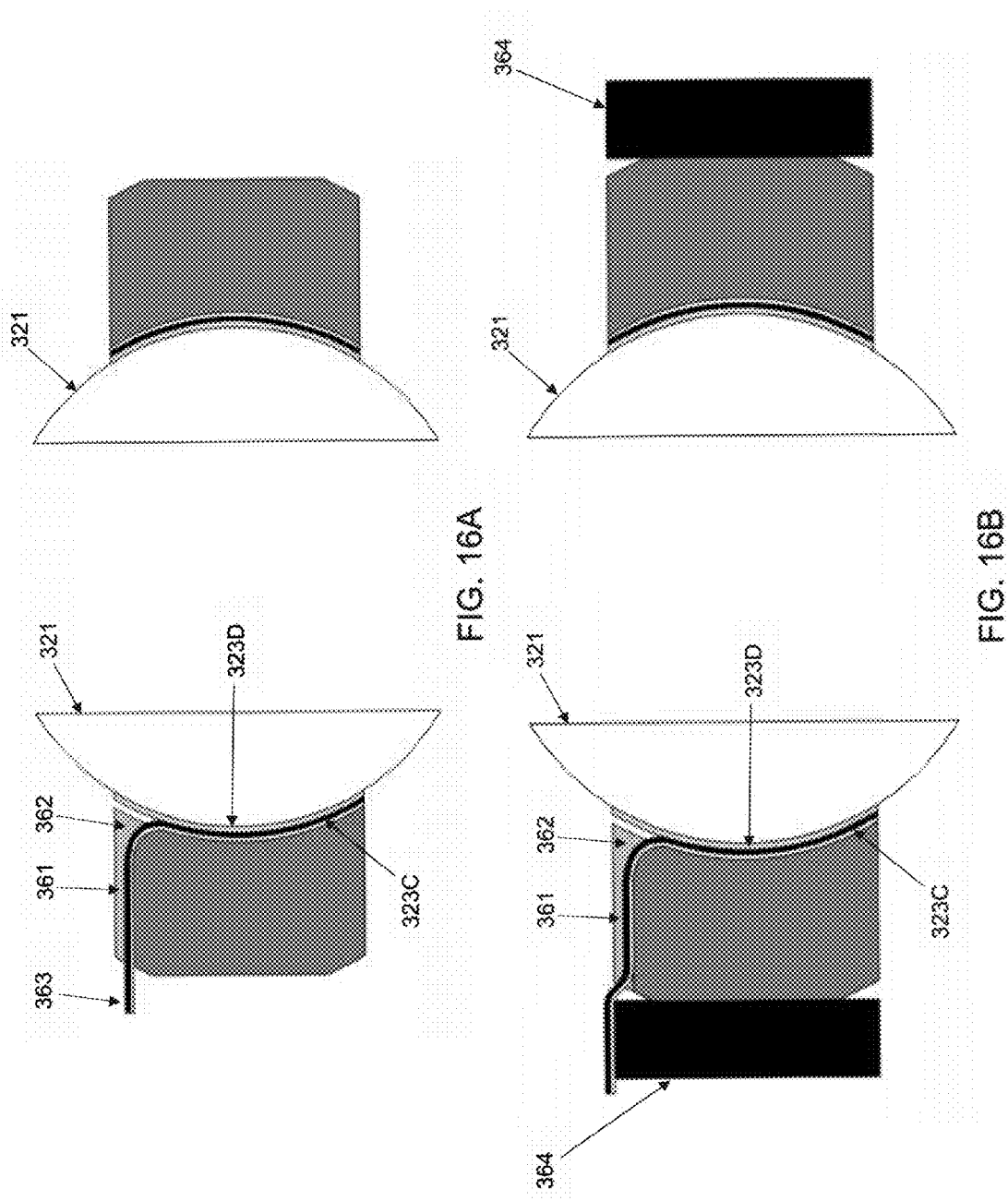

SENSOR FOR WEAR MEASUREMENT, METHOD FOR MAKING SAME, AND METHOD FOR OPERATING SAME

REFERENCE TO PENDING PRIOR PATENT APPLICATIONS

This patent application:

(i) is a continuation-in-part of pending prior U.S. patent application Ser. No. 14/054,447, filed Oct. 15, 2013 by NanoLab, Inc. and Iosif Izrailit et al. for SENSOR FOR WEAR MEASUREMENT, METHOD OF MAKING, AND METHOD OF OPERATING SAME, which patent application claims benefit of prior U.S. Provisional Patent Application Ser. No. 61/713,735, filed Oct. 15, 2012 by NanoLab, Inc. and Iosif Izrailit et al. for SENSOR FOR WEAR MEASUREMENT, METHOD OF MAKING, AND METHOD OF OPERATING SAME; and (ii) claims benefit of prior U.S. Provisional Patent Application Ser. No. 61/898,128, filed Oct. 31, 2013 by NanoLab, Inc. and David L. Carnahan et al. for SENSOR FOR WEAR MEASUREMENT, METHOD OF MAKING, AND METHOD OF OPERATING SAME.

The three (3) above-identified patent applications are hereby incorporated herein by reference.

This invention was made with Government support under N68335-13-C-0203 awarded by the Department of the Navy. The Government has certain rights in this invention.

FIELD OF THE INVENTION

This invention relates to bearings in general, and more particularly to bearings that employ a low-friction wear lining material instead of balls or rollers to support a load. Even more particularly, this invention relates to sensors adapted to measure wear in bearings that employ a low-friction wear lining material.

BACKGROUND OF THE INVENTION

Bearings are widely used to support a load. Some bearings use balls or rollers to support the load. Other bearings use a low-friction wear lining material to support the load.

Where the bearings use a low-friction wear lining material to support the load, it can be advantageous to provide the bearing with sensors which measure wear in the low-friction wear lining material.

U.S. patent application Ser. No. 14/054,447, which is incorporated herein by reference, relates to bearings which use a low-friction wear lining material to support a load, and to the provision and use of sensors for measuring wear in the low-friction wear lining material. Among other things, U.S. patent application Ser. No. 14/054,447 relates to the electrical measurement of capacitance (or other electrical parameters) between a movable surface and an electrode, which electrode may be positioned within (or on) the back side of the low-friction wear lining material, and to the correlation of the electrical measurement of capacitance (or other electrical parameters) to the wear of the low-friction wear lining material, whereby to determine wear in the low-friction wear lining material.

SUMMARY OF THE INVENTION

The present invention comprises the provision and use of sensors for measuring wear in bearings, and to the construction and use of bearings incorporating such sensors. Among other things, the present invention relates to the various materials, treatments, adhesives, methods and structures that can be used to form wear sensors in bearings utilizing low-friction wear lining materials.

In one preferred form of the invention, there is provided a spherical bearing comprising:
 a race;
 a ball;
 a wear lining; and
 a capacitive sensor positioned within or behind the wear lining to gauge wear of said wear lining.

In another preferred form of the invention, there is provided a method for installing a sensor-equipped spherical bearing, the method comprising:
 placing a sensor lead of the sensor-equipped spherical bearing out of the path of a compression tool used to deform a metal surrounding a staking groove to fixate a race of the spherical bearing within a housing; and
 thereafter affixing said sensor lead to said race and housing after the compression tool has been used to deform a metal surrounding a staking groove.

In another preferred form of the invention, there is provided a method for making electrical contact to the wear sensor capable of surviving prolonged vibration, the method comprising:
 providing a substrate that is affixed to a component, a sensor lead of the wear sensor passing underneath said substrate, said substrate comprising metallized vias through or around said substrate that connect said sensor lead to electrical traces on said substrate which also contact a connector on said substrate.

In another preferred form of the invention, there is provided a method for making electrical contact to a wear sensor in a bearing assembly comprising a race, the method comprising:
 providing a hole in said race; and
 inserting an insulated electrical lead into said hole in said race so that the one end of said insulated electrical lead contacts an electrode of said wear sensor.

In another preferred form of the invention, there is provided a rod end construction, the rod end construction comprising:
 a ball;
 a wear liner;
 a wear sensor;
 a housing; and
 a connector.

In another preferred form of the invention, there is provided a washer for use with a rod end construction, the washer comprising:
 a toroid having a rectangular cross-section;
 an internal key or tab that protrudes into the inner diameter of said toroid; and
 an electrical contact and lead passing radially through said washer to enable the washer to electrically connect a sensor lead within said internal key or tab to the outside world.

BRIEF DESCRIPTION OF THE DRAWINGS

These and other objects, features and advantages of the present invention will be more fully disclosed or rendered obvious by the following detailed description of the preferred embodiments of the invention, which is to be considered together with the accompanying drawings wherein like numbers refer to like parts and further wherein:

FIG. 1A illustrates a new sleeve bearing with a sensor inserted into a wear liner in accordance with the present invention;

FIG. 1B illustrates a symmetrically worn sleeve bearing with a sensor inserted into a wear liner in accordance with the present invention;

FIG. 1C illustrates a non-concentrically worn sleeve bearing with a sensor inserted into a wear liner in accordance with the present invention;

FIGS. 2A-2D illustrate a sleeve bearing with a capacitive sensor inserted into a wear liner in accordance with the present invention, wherein the capacitive sensor is intended to be measured with a probe contact;

FIGS. 3A-3D illustrate a sleeve bearing with a capacitive sensor inserted into a wear liner in accordance with the present invention, wherein the sleeve bearing comprises an antenna with significant inductance for creating a resonant LC circuit;

FIGS. 4A-4D illustrate a spherical bearing with a capacitive sensor inserted into a wear liner in accordance with the present invention, wherein the capacitive sensor is intended to be measured with a probe contact;

FIGS. 5A and 5B illustrate a method of interrogating a capacitive sensor inserted into a wear liner of a spherical bearing in accordance with the present invention, wherein the capacitive sensor is intended to be interrogated using a capacitance meter;

FIGS. 6A-6D illustrate a spherical bearing with a capacitive sensor inserted into a wear liner in accordance with the present invention, wherein the spherical bearing comprises an antenna with significant inductance for creating a resonant LC circuit;

FIGS. 7A and 7B illustrate a method for interrogating the capacitive sensor shown in FIGS. 6A-6D with a tracking generator, matching network, interrogating antenna, and spectrum analyzer;

FIG. 8A illustrates a new square telescoping bearing with a sensor inserted into a wear liner in accordance with the present invention;

FIG. 8B illustrates a worn square telescoping bearing with a sensor inserted into a wear liner in accordance with the present invention;

FIGS. 9A-9C depict a process for producing a wear liner formed in accordance with the present invention;

FIGS. 14A and 14B are schematic views showing two features useful for installing the capacitive sensor, the first being a chamfer to reduce the angle that the sensor lead must traverse, and the second being a radial slot that is deeper than the staking groove;

FIGS. 15A and 15B are schematic views showing how the sensor lead is held out of the way before and during the installation operation (FIG. 15A), and then laid over after the installation operation (FIG. 15B);

FIGS. 16A and 16B are schematic views showing how the sensor lead is routed to the edge of the bearing through a radial groove on the surface of the race of the bearing, to enable a standard compression tool to be used for bearing insertion.

DETAILED DESCRIPTION OF THE PREFERRED EMBODIMENTS

Figure 10:
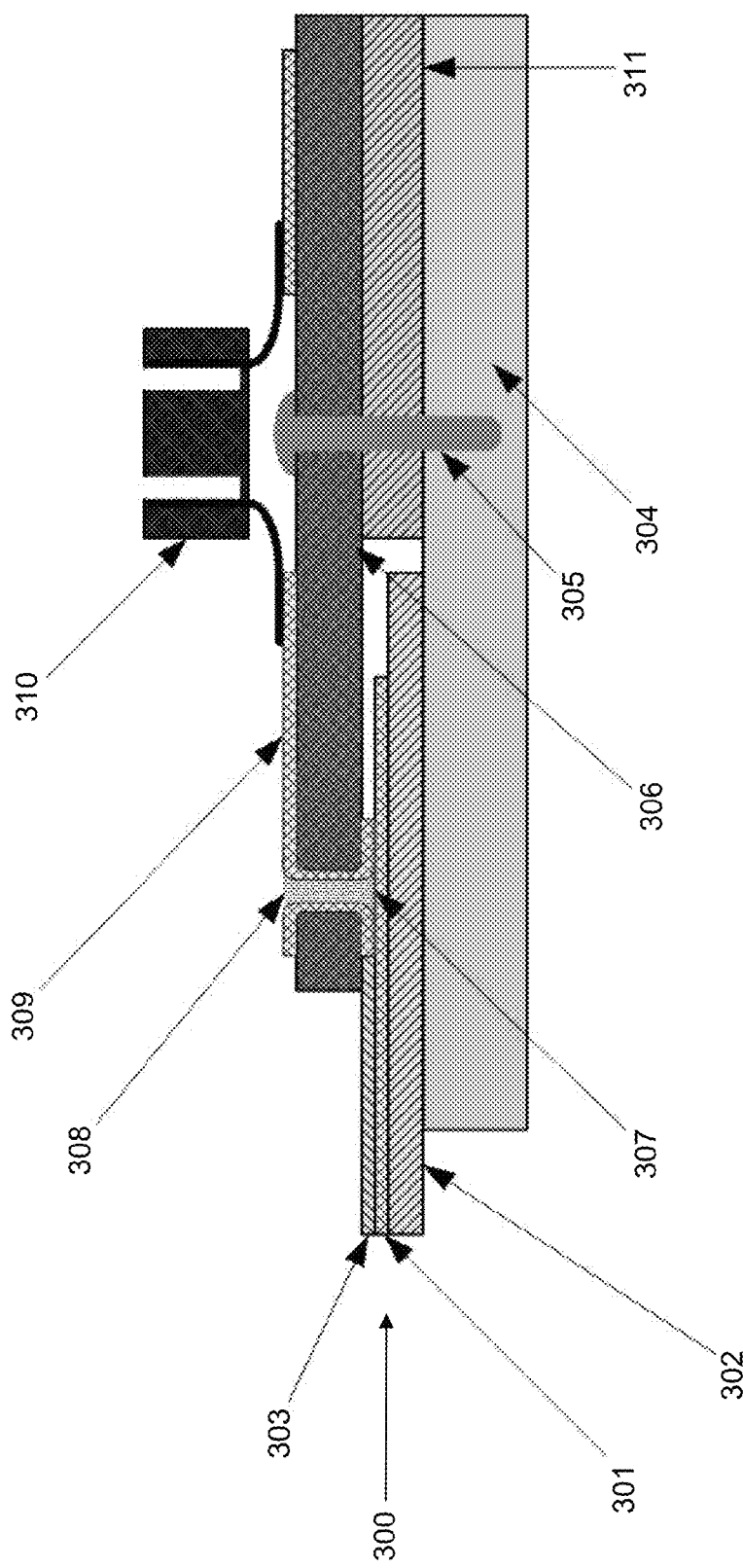
FIG. 10 is a schematic view showing a novel approach for attaching a sensor lead to a fixed surface.

The present invention comprises an insulating wear liner with a sensor that is positioned either within the liner or placed on the non-wearing surface of the liner. The sensor comprises a conductive electrode and one or more pads for interrogating the electrical properties of the sensor. The liner is situated between the race of the bearing and the moving part.

By way of example but not limitation, a sensor may be positioned inside of the wear liner of a sleeve bearing, and the capacitance between the wear liner and the shaft can be calculated for the "new" condition of the shaft and wear liner. Subsequently, after wear of the wear liner by the shaft, the capacitance between the wear liner and the shaft can be calculated for the "worn" condition.

Looking now at FIG. 1A, there is shown a new sleeve bearing having a sensor inserted into the wear liner according to the present invention.

The new, unused sleeve bearing is assembled with a shaft which has radius $R_{shaft}$. The shaft is centered in the bearing, concentric with the race of the bearing, which has a radius $R_{race}$. The conductive electrode of the sensor is positioned inside the liner, having radius $R_{sensor}$, such that the race of the bearing, the conductive electrode of the sensor and the shaft are arranged concentrically, with $R_{race} > R_{sensor} > R_{shaft}$.

Assume that the liner has a uniform dielectric constant of $\varepsilon$. The new bearing, prior to incurring wear, will have a capacitance $C_{new}$ between the conductive electrode of the sensor and the shaft, which capacitance is given by the equation:

$$C_{new} = \frac{2\pi\varepsilon_0\varepsilon}{\ln(R_{sensor}/R_{shaft})}$$

Table 1 shows a calculation of capacitance for an exemplary new shaft bearing.

TABLE 1

Calculation of capacitance for new liner in a sleeve bearing

| NEW LINER | | inch | Value | Metric Unit |
|---|---|---|---|---|
| Wear liner thickness | T | 0.012 | 0.00030 | m |
| sensor position | Sp | 0.006 | 0.00015 | m |
| Diameter of Shaft | Dsh | 0.500 | 0.01270 | m |
| Diameter of Race | Dr = Dsh + 2T | 0.524 | 0.01331 | m |
| Diameter of Sensor | Ds = Dsh + 2Sp | 0.512 | 0.01300 | m |
| Bearing Length | L | 0.500 | 0.01270 | m |
| Dielectric constant of liner | e | 2 | 2 | |
| Permittivity of vacuum | e0 | | 8.85E−12 | F/m |
| Radius of shaft | Rsh = Dsh/2 | | 0.00635 | m |
| Radius of race | Rr = Dr/2 | | 0.00665 | m |
| Radius of sensor | Rs = Ds/2 | | 0.00650 | m |
| Capacitance sensor-shaft | C = 2*pi*e*e0/ (ln(Rs/Rsh)) | | 4689.2 | pF/m |
| Capacitance Bearing, pF | Cb = C*L | | 59.6 | pF |

There will also be capacitance between the conductive electrode of the sensor and the outer race of the bearing, but this capacitance value should remain constant over the life of the bearing. Between the conductive electrode of the sensor and the moving shaft, wear will occur. Accordingly, the thickness of the wear liner will decrease, and the shaft will exhibit more play. One aspect of the present invention is the effect of concentricity on the measured capacitance of a sensor embedded in a wear lining. It should be appreciated that two wear modes can occur, i.e., concentric uniform wear or non-concentric non-uniform wear.

To illustrate uniform wear, consider a bearing that is worn with perfect symmetry so that some of the wear liner is removed from its entire circumference. Next, position the shaft in perfect concentricity with the race and sensor electrode. FIG. 1B illustrates a symmetrically worn sleeve bearing with a sensor inserted into the wear liner according to the present invention.

In this arrangement, there are two capacitors in series, one made of air, $C_{air}$, and another made from the remaining liner, $C_{liner}$. The air gap, having thickness W, will have a capacitance based on the radial gap, $R_{liner}=R_{shaft}+W$. The capacitance of that gap may be represented by the equation:

$$C_{air} = 2\pi\varepsilon_0\left(\frac{\varepsilon_{air}}{\ln((R_{shaft}+W)/R_{shaft})}\right)$$

Likewise, the wear liner will have a capacitance based on its thickness, equal to $R_{sensor}-R_{liner}$, or $R_{sensor}-(R_{shaft}+W)$:

$$C_{liner} = 2\pi\varepsilon_0\left(\frac{\varepsilon_{liner}}{\ln(R_{sensor}/(R_{shaft}+W))}\right)$$

The total capacitance, $C_T$, will follow that of two capacitors in series: $C_T=(C_{air}\times C_{liner})/(C_{air}+C_{liner})$. Table 2 shows the result of this calculation.

TABLE 2

Concentrically worn sleeve bearing

| CONCENTRIC WEAR | | inch | Value | Metric Unit |
|---|---|---|---|---|
| Wear liner thickness | T | 0.012 | 0.000305 | m |
| sensor position | Sp | 0.006 | 0.000152 | m |
| Diameter of Shaft | Rsh = Dsh/2 | 0.500 | 0.012700 | m |
| Diameter of Race | Rr = Dr/2 | 0.524 | 0.013310 | m |
| Diameter of Sensor | Rs = Ds/2 | 0.512 | 0.013005 | m |
| Bearing Length | L | 0.500 | 0.012700 | m |
| Dielectric constant of liner | e | 2 | 2 | |
| Permittivity of vacuum | e0 | | 8.85E−12 | F/m |
| Radius of shaft | Rshaft | | 0.00635 | m |
| Radius of race | Rr | | 0.00665 | m |
| Radius of sensor | Rsensor | | 0.00650 | m |
| Wear | W | 0.004 | 0.00010 | m |
| Radius of liner | Rliner = Rshaft + Wear | | 0.00645 | m |
| Capacitance shaft to liner | Cair = 2*pi*e0(1/ln(Rliner/Rshaft) | | 3503 | pF/m |
| Capacitance liner to electrode | Cliner = 2*pi*e0(e/ln(Rsensor/Rliner) | | 14180 | pF/m |
| Total Capacitance/m | CT = (Cair*Cliner)/(Cair + Cliner) | | 2809 | pF/m |
| Capacitance | C = CT*L | | 35.7 | pF |

The resulting capacitance is lower than the value calculated in Table 1 for the new bearing. Note that this is the case only if the shaft is held at the center. If loaded, the shaft will be non-concentric as discussed below.

Next, to illustrate the non-concentric, non-uniform case, consider a bearing that has been loaded and worn preferentially on one side. The result is that the shaft is no longer concentric with the sensor. FIG. 1C illustrates a non-concentrically worn sleeve bearing with a sensor inserted into the wear liner according to the present invention.

The capacitance of two cylinders eccentrically located one inside the other with radii ($R_{shaft}$) and ($R_{sensor}$), respectively, but with the centers of the two cylinders having a distance (W) apart, will be larger than in the concentric case. Ignoring the replacement of the worn-away dielectric with air, the capacitance may be represented by the equation:

$$C = 2\pi\varepsilon_0\varepsilon\left(\frac{1}{\mathrm{acosh}(-(W^2-R_{shaft}^2-R_{sensor}^2)/2R_{shaft}R_{sensor})}\right)$$

The capacitance is calculated for an eccentrically worn sleeve bearing in Table 3.

TABLE 3

Non-concentric wear of a sleeve bearing

| WORN LINER | | inch | Value | Metric Unit |
|---|---|---|---|---|
| Wear liner thickness | T | 0.012 | 0.000305 | m |
| sensor position | Sp | 0.006 | 0.000152 | m |
| Diameter of Shaft | Dsh | 0.500 | 0.012700 | m |
| Diameter of Race | Dr = Dsh + 2T | 0.524 | 0.013310 | m |
| Diameter of Sensor | Ds = Dsh + 2Sp | 0.512 | 0.013005 | m |
| Bearing Length | L | 0.500 | 0.012700 | m |
| Dielectric constant of liner | e | 2 | 2 | |
| e0 | e0 | | 8.85E−12 | F/m |
| Radius of shaft | Rsh = Dsh/2 | | 0.006350 | m |
| Radius of race | Rr = Dr/2 | | 0.006655 | m |
| Radius of sensor | Rs = Ds/2 | | 0.006502 | m |
| Eccentric Wear | W | 0.004 | 0.000102 | m |
| Capacitance/m shaft to sensor | C = 2*pi*e*e0*(1/(acosh(−(W^2 − Rsh^2 − Rs^2)/2Rsh*Rs)) | | 6440.4 | pF/m |
| Capacitance of Bearing | Cb = C*L | | 81.8 | pF |

In Table 3, it will be seen that the capacitance is significantly higher for the non-concentric worn bearing than for the new (i.e., non-worn) bearing. A notable aspect of the present invention is that the capacitance between a metallic shaft and a sensor placed inside or behind the wear liner will increase with concentric or non-concentric wear, as long as the shaft is loaded. The capacitance is an inverse function of the liner thickness. Accordingly, the capacitance increases rapidly as the liner thickness approaches zero.

With respect to the two wear conditions discussed above (i.e., concentric uniform wear or non-concentric non-uniform wear), it has been found that the non-uniform, non-concentric condition is more prevalent, since the loading and wear of bearings is rarely uniform. As such, the wear of a bearing can be correlated to a measurable increase in capacitance between the shaft and the sensor.

The capacitance measurement can be made at different frequencies. A standard frequency for capacitance measurement is 10 kHz. Measurements taken at a higher frequency improve the sensitivity of the measurement, but also increase the error due to interference. The optimal frequency for accuracy will depend on the electromagnetic interference in the environment surrounding the bearing. The measurement of Q factor, which can be calculated from the active and inductive current components in the sensor, provides information about the status of the liner. If at any point the gap between the sensor and the moving part (e.g., ball, shaft, etc.) approaches zero, Q will drop rapidly toward zero. It will also be electrically shorted at this point. A Q under 5 indicates that the bearing needs immediate replacement, and a Q above 20 indicates a bearing with good health. The electrical shorting of the sensor and the moving part (e.g., ball, shaft, etc.) can also be used as an indicator that the wear liner has failed in at least one spot, and therefore needs replacement.

Turning again to FIGS. 1A, 1B and 1C, FIG. 1A illustrates a new sleeve bearing (without wear) 200, comprising an outer race 201, a movable shaft 203, a wear liner 206 and a sensor 205 inserted into wear liner 206.

FIG. 1B illustrates the sleeve bearing 200 of FIG. 1A after symmetric wear of wear liner 206. The symmetric wear of wear liner 206 results in a worn sleeve bearing 200 having an air gap 222 which is equally spaced around its circumference from wear liner 206 and movable shaft 203.

FIG. 1C illustrates an asymmetrically, non-concentrically worn sleeve bearing 200 with a sensor 205, where the air gap 222 between shaft 203 and sensor 205 (resulting from removal of some of wear liner 206 due to wear) is closer to sensor 205 in one location than in another location.

Looking now at FIGS. 2A-2D, there is shown a sensor 205 for a sleeve bearing 200, comprising a race 201, a shaft 203, a sensor 205 and a wear liner 206. Sensor 205 comprises a conductive trace 208 which is sandwiched between first and second layers 209 formed out of insulating substrate (FIG. 2B) which may be of differing thicknesses. When sensor 205 is laid flat (FIG. 2C), conductive trace 208 can be seen in detail, along with tabs 210 that extend from sleeve bearing 200. Electrode pads 213 are positioned on the surface of tabs 210, and can be probed with a capacitance meter to measure the capacitance between one electrode pad and shaft 203 (FIG. 2D).

Looking now at FIGS. 3A-3D, there is shown a sensor 205 for a sleeve bearing 200. Sleeve bearing 200 comprises a race 201, a shaft 203, a sensor 205 and a wear liner 206. Sensor 205 comprises a conductive trace 208 sandwiched between a first layer of insulating substrate 209 and a second layer of insulating substrate 214 (FIG. 3B). When sensor 205 is laid flat (FIG. 3C), conductive trace 208 can be seen in detail, along with tabs 210 that extend from sleeve bearing 200. Electrode pads 213 are positioned on the surface of tabs 210 which can be taken together as a connection point 220 for an antenna 221.

FIGS. 4A-4D illustrate a spherical bearing 200 comprising a race 201, a ball 202, a shaft 203, a sensor 205, a wear liner 206 and an insulator 207. Sensor 205 comprises a conductive trace 208 sandwiched between two layers of insulating substrate 209 (FIG. 4B). When sensor 205 is laid flat (FIG. 4C), conductive trace 208 can be seen in detail, along with tabs 210 that extend from sleeve bearing 200. Strain relief cuts 212 formed on sensor 205 enable sensor 205 to deform into a more conforming shape. Electrode pads 213 are positioned on the surface of tabs 210 for the interrogation of sensor 205 (FIG. 4D). Viewed end on, after installation, electrode pads 213 may be touched with one probe of a capacitance meter.

Looking now at FIGS. 5A and 5B, there is shown a method of interrogating sensor 205. As shown in FIG. 5A, a probe 225 of a precision capacitance meter 230 makes contact with an electrode pad 213 on the circumference of spherical bearing 200. Assuming that race 201 and shaft 203 are both conductive and electrically connected elsewhere, the capacitance measured by the precision capacitance meter will comprise the capacitance between ball 202 and sensor 205, which is electrically in series with the capacitance between sensor 205 and race 201.

FIGS. 6A-6D illustrate a spherical bearing 200 comprising a race 201, a ball 202, a shaft 203, a sensor 205, a wear liner 206 and an insulator 207. Sensor 205 comprises a conductive trace 208 sandwiched between two layers of insulating substrate 209 (FIG. 6B). When sensor 205 is laid flat (FIG. 6C), conductive trace 208 can be seen in detail, along with tabs 210 that extend from sleeve bearing 200. Strain relief cuts 212 formed on sensor 205 enable sensor 205 to deform into a more conformal shape. Electrode pads 213 are positioned on the surface of tabs 210 for the interrogation of the sensor (FIG. 6D). Viewed end on, after installation, tabs 210 and electrode pads 213 are connected at a point 220 to an antenna 221, which may be mounted on the face of race 201.

Looking now at FIGS. 7A and 7B, there is shown a method of interrogating sensor 205 wirelessly. A signal produced by a tracking generator 235 is coupled through a matching network 240 to a loop antenna 245, which interacts with sensor antenna 221, for measuring bearing wear remotely. The output frequency of tracking generator 235 is varied over time, and at one moment will match the frequency of the LC circuit created by the sensor's capacitance and the antenna's inductance. At that moment, a spectrum analyzer 250 will detect the resonance frequency. The shift in resonant frequency due to the change in sensor capacitance will correspond to the reduction in the wear liner thickness.

FIG. 8A illustrates a new square telescoping bearing with a sensor inserted into the wear liner in accordance with the present invention.

FIG. 8B illustrates a worn square telescoping bearing with a sensor inserted into the wear liner in accordance with the present invention.

One illustrative procedure for producing a device according to the present invention is shown in FIGS. 9A-9C. In FIG. 9A, there is shown an insulating substrate 209 with a metallic coating 208. In FIG. 9B, a second layer of insulator 214 is applied to metallic coating 208 so as to sandwich the electrode (i.e., metallic coating 208) between insulating substrate 209 and insulator 214. If desired, metallic coating 208 may be patterned. Optionally in FIG. 9C, a pattern is cut out, producing a sensor that can be inserted into a spherical bearing.

Looking again at FIGS. 8A and 8B, FIG. 8A is an end-view of a new, un-worn telescoping structure comprising an outer sleeve 201, an inner shaft 203 and a wear lining 206, which has been instrumented with a sensor 205 partway through wear lining 206. In FIG. 8B, wear liner 206 has been worn, leaving an air gap 222 and a lining having a reduced thickness on one side. The capacitance of this system can be modeled as the sum of the four parallel plate capacitors. Capacitance in this system is equal to the product of the permittivity of free space $\epsilon_0$, the dielectric constant $\epsilon$ and the area A divided by the distance d:

$$C = \epsilon \epsilon_0 A/d.$$

Comparing FIG. 8A to FIG. 8B, the lining thickness on the sides is unchanged, but in FIG. 8B the upper and lower distances are changed. At the bottom, the thickness of wear lining 206 has been reduced by wear, and a corresponding air gap 222 has opened up above shaft 203 at the top. The upper capacitor will have a lower value than before inasmuch as the distance between shaft 203 and sensor 205 is increased by air gap 222. The lower capacitor will have a much higher value than before, inasmuch as it has a distance between shaft 203 and sensor 205 that is reduced by the same distance as air gap 222. The increase in capacitance for the lower capacitor will more than make up for the decrease in capacitance for the upper capacitor. This is clear because the function 1/d is nonlinear. It approaches infinity as the quantity "d" gets small, and it approaches zero as the quantity "d" gets large.

It should be appreciated that a similar type of measurement could be made if the wear liner material is conductive and the resistance is measured as a function of wear.

It should also be appreciated that there are two methods which may be used to measure the capacitance of the sensor. The first method is to measure the value directly with a probe and a capacitance meter. The other method is to measure the resonant frequency of the combination of the sensor's capacitance and the attached antenna's inductance. A similar measurement could be implemented using an inductive sensor and a distributed capacitor to create the resonant circuit.

The preceding examples should be construed as non-limiting, as other methods of implementing the sensor are possible. Also, other methods can be used to measure the wear in addition to capacitance, including inductance and resistance.

Additional aspects of the present invention are discussed below.

Substrates

A number of different substrate materials can used with the present invention, e.g., to form insulating substrate 209, insulating substrate 214, etc. For example, polyimide films such as DuPont's Kapton™ and its metallized version Pyralux™, which are commonly used for flexible electronics due to the material's high melting point and chemical resistance, may be utilized with the present invention. Or the sensors of the present invention may be produced using any other suitable insulating substrate material. Non-limiting examples of flexible substrate materials that can be used with the present invention include: urethanes, polyesters (PET), polyimides (PI), polyethylene napthalates (PEN), and polyetherimides (PEI), along with various fluropolymers (FEP) such as Teflon and copolymers. Materials from companies such as Porex of Fairburn, Ga. (Porex films) and AIT of Princeton Junction, N.J. (Coupler-MIP) are suitable replacements for the Pyralux films discussed above. Polyonics, Inc. of Westmoreland, N.H. also produces polyimide-based flexible substrates, such as their XF107 product and other offerings.

Layup

Sensors for the measurement of capacitance and other electrical parameters that change with wear can be made from a metallized insulating substrate. An optional second layer of an insulating material can be added on top of the metallized substrate to further seal or protect the metallization. This requires an adhesive to bond the metallization to the bottom side of the second layer of insulating material.

Treatments

A number of treatments can be applied to the polymeric substrate materials to improve their compatibility with various adhesives, which are used to bond the sensor in place. By way of example but not limitation, such treatments may include corona and plasma treatment (with air, oxygen and/or other gases), abrading or roughening of the surface chemically, mechanically or ultrasonically, heat treating the substrate, and etching the substrate surface with a solvent, acid, base, peroxide, or other chemical etchant. These treatments are well known in the art and are sometimes used industrially to improve the "bite" of adhesives or coatings to substrates.

Resin Adhesives

A number of resin materials may be used as the adhesive to bond the sensor to the support and to bond the sensor to the wear liner. Some favored resin materials are one-component, thermosetting-type adhesive materials. By way of example but not limitation, thermosetting-type resins may include epoxy resins, urethane resins and phenolic resins, or modifications thereof, such as hardenable cross-linkable vinyl-phenolic resins, which cure, thermoset, cross-link or harden with the application of pressure and/or heat over a given length of time. The curing cycle may be interrupted so that the resin binder is not fully set or cross-linked during the initial forming, in order to permit additional manufacturing steps to be conducted before hardening the composition completely.

Fenner Precision of Buffalo, N.Y. produces a number of "pre-preg" adhesive and liner compositions that may be used with the present invention.

Other adhesives that can be used with the present invention include, but are not limited to, the following:

(i) Adhesives in sheet form, and applied to the back of the sensor. One such adhesive film is the RM-1005 adhesive film of Renegade Material of Miamisburg, Ohio, which has a maximum use temperature of 316 degrees C.

(ii) 3M of St. Paul, Minn. also has a series of adhesives suited to aerospace use that can be applied to bond the sensors to races and bond the sensors to liner materials. 3M's product AF191, for example, is a thin sheet adhesive commonly used for honeycomb sandwich panel construction. It is available in a 2.5 mil thickness sheet, which will cure at 177 degrees C. in one hour. However, in practice, thinner adhesive bond-lines are preferred for bearing use, so the use of liquids that are either paintable or spray-able is common. 3M's offerings also include Scotch-Weld™ Epoxy Adhesive EC-3710, which is the spray-able version of the AF 191 product. 3M's primer line may be used to improve adhesion to stainless steels and other substrates.

(iii) Maverick Resins Corp. of Blue Ash, Ohio, manufactures a number of resins that can be used with the present invention. By way of example but not limitation, MVK 7000 (compression moldable vinyl phenolic resin) may be used with the present invention. AFR-PE-4 (autoclaveable or compression moldable thermosetting polyimide resin) may also be used with the present invention. Note that AFR-PE-4 does not contain the toxic diamine 4,4'-methylenedianiline (MDA) or any other mutagenic or carcinogenic components. MVK-19 (compression moldable polyimide resin may also be used with the present invention. Note that MVK-19 is also MDA free and carcinogenic/mutagenic component free.

With recent increased concern over the use of toxic chemicals, it may be beneficial to use a binder material that was compliant with US and International environmental standards (such as RohS and REACH).

Integration

The connection of a measurement device to interrogate the wear sensors can be achieved by both hard-wired and wireless means, as will hereinafter be discussed.

In one form of the invention, a soldered connector contact may be used to connect a measurement device to the wear sensor so that the measurement device can interrogate the wear sensor. More particularly, the electrode trace material in the sensors is preferably copper, as copper is widely available, but any other appropriate conductor may be used as the electrode material. Preferably, the conductor is over-coated with a thin layer of a polymeric film to protect the conductor from corrosion. The only exposed areas of the sensor are where the sensor must interface with the measurement device. These are preferably gold-coated to ensure a non-tarnishing contact, with a solder-wettable surface. There are a number of methods to make contact to the electrode, including probe contact (for intermittent measurements), or mechanical or soldered contacts (for permanent installations).

Looking now at FIG. 10, a sensor lead 300, comprising a sensor metallization 301, a sensor substrate 302, and a sensor top coating 303, may be mounted on a structure 304 by means of a screw 305 or other means (e.g., an adhesive). Sensor lead top coating 303 is stripped back where sensor lead 300 is inserted beneath a connector board 306. This allows a solder connection 307 to be made through the connector board 306 by means of a via 308, thereby electrically connecting board metallization 309 to sensor lead 300. Board metallization 309 can then be attached to a connector 310 so as to enable attachment to an external measurement device. An optional spacer (or adhesive layer) 311 can be inserted below connector board 306 so as to stabilize the assembly. Spacer 311 may not be necessary if the sensor lead 300 is adhered to a recess in the structure of similar thickness to the sensor lead. The assembly may then be oversprayed with a sealant to protect and insulate the exposed leads, except where connector 310 must make external electrical contacts (e.g., to connect to an external measurement device).

Other methods for making a connection between the flexible electronics and the connector are known and commonly practiced in the industry. Edge-on connectors, where the lead is inserted into a connector and then soldered, are common, but edge-on connectors suffer from poor reliability in high vibration environments, particularly where the lead is not fully supported. In the attachment scheme of FIG. 10, the lead 300 is fully supported along its entire length, thereby making it more vibration resistant. Accordingly, one aspect of the present invention is the provision of a vibration-tolerant connection between the flexible electronic sensor lead 300 and an electronic connector (e.g., connector 310).

In some situations, a ball may be inserted into a housing to make a rod end. For this situation, the present invention provides an effective and elegant solution for enabling the connection of the wear sensor to the outside world. More particularly, it is common for rod ends to have a groove cut in the threaded portion of the rod to accept a key, whereby to prevent the rod end from rotating after being installed. In accordance with the present invention, it has been discovered that the groove in the rod end may also be used to route the sensor lead to a connector, which can be installed in a specially-designed washer or nut.

Figure 11C:
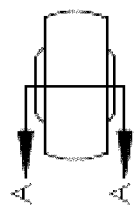
FIGS. 11A-11D are schematic views showing a rod end modified to accept a sensor.
Figure 11A:
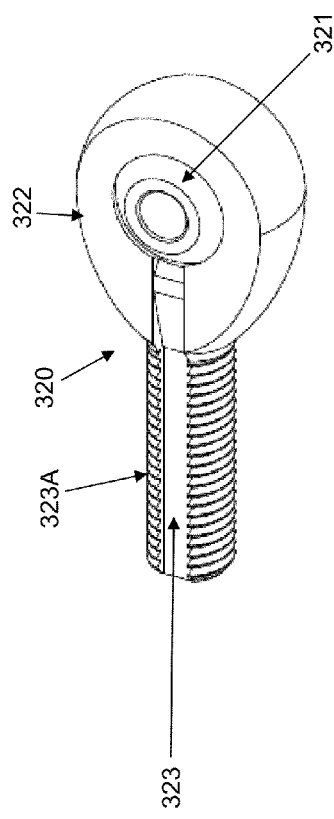
Figure 11B:
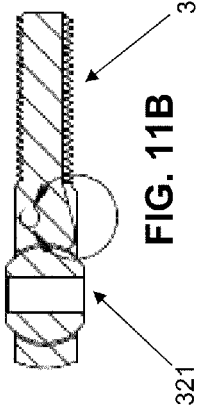
Figure 11D:
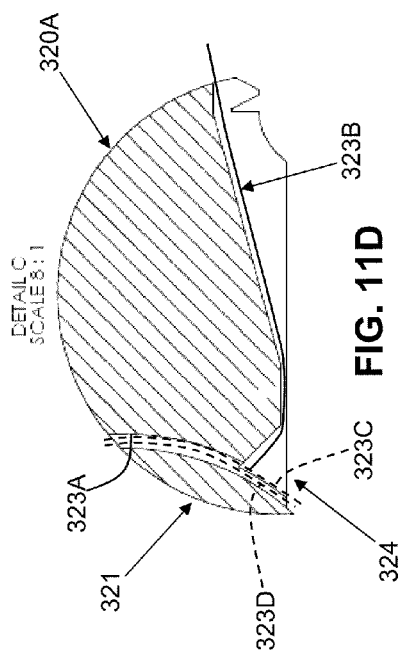

By way of example but not limitation, in FIGS. 11A-11D, there is shown a modified rod end 320 comprising a rod 320A, a ball 321, and a housing 322 secured to rod 320A and capturing ball 321 within housing 322. Rod 320A preferably comprises a threaded end portion having a keyway 323 cut in the threads to accept a key. In one form of the present invention, modified rod end 320 comprises a tapered channel 324 that connects keyway 323 to the race of the bearing (i.e., the surface 323A of rod 320A), so that a sensor lead 323B can be routed from sensor electrode 323C through tapered channel 324. Wear liner 323D is positioned between ball 321 and sensor electrode 323C. A key to this implementation is the requirement that the sensor lead not make sharp turns (e.g., turns greater than or equal to 90 degrees over a short distance) as it passes through tapered channel 324 and keyway 323. A channel running the complete length of the rod (as shown in FIG. 11A) is not necessary, i.e., the taper may terminate at the face of the housing, but chamfering/filleting of any sharp angles is generally required. The preferred embodiment of this structure has a minimum radius of curvature for the sensor material that is equal to 10× the sensor thickness.

Figure 12C:
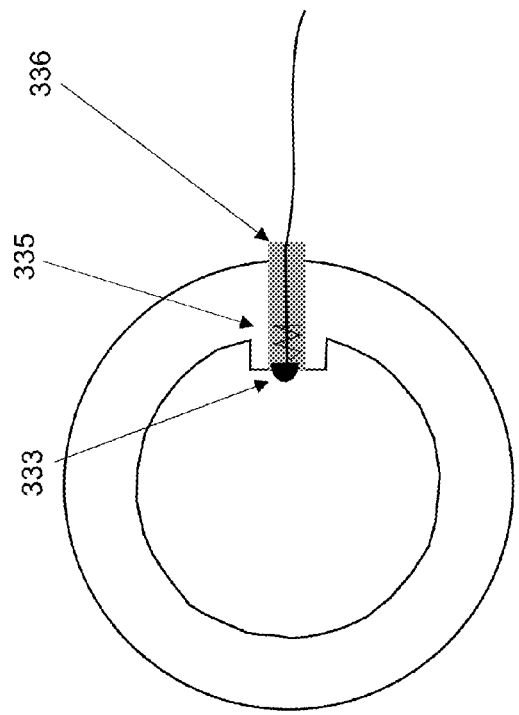
FIGS. 12A-12C are schematic views showing a contact for the wear sensor, wherein the contact includes a tab washer with an internal electrical contact and wire.
Figure 12B:
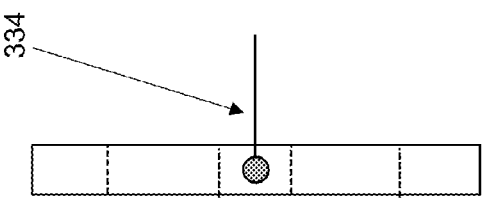
Figure 12A:
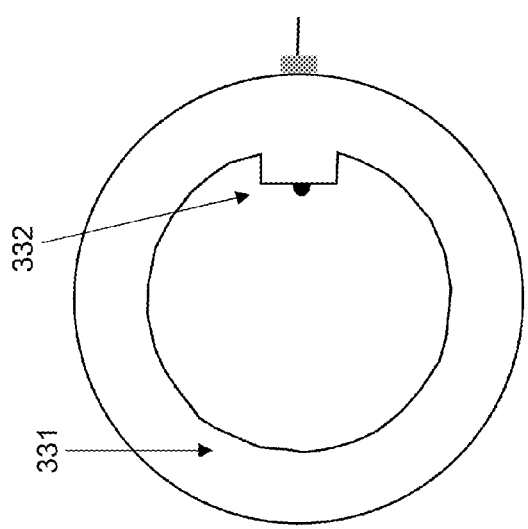

One aspect of the present invention is to provide a way in which the sensor lead can be connected to an external analyzer. Any connection for use in high vibration environments must be tolerant of the issues associated with high vibration environments. One method by which the sensor signal can be extracted from the sensor lead disposed in a channel (e.g., sensor lead 323B disposed in channel 324 and keyway 323) is to provide a contact within a washer or nut. FIGS. 12A-12C show a washer 331 that has been modified with a contact. More particularly, washer 331 is a modified form of an internal tab washer, and comprises a single internal (inwardly-facing) tab 332 that is designed to fit in the channel 323 which is formed in a rod end so as to prevent rotation of the rod. Washer 331 has been modified to provide an electrical contact 333 that will, on one end, contact the sensor lead electrode disposed in channel 323, and on the other end terminate in a sensor lead (e.g., a wire) 334 for carrying the signal to a readout device. In this example, an internal ball spring plunger 335 is used to make the electrical contact between the wire and the sensor lead electrode (which is disposed in channel 323). Housing 336 of the contact must be electrically insulating. An alternative embodiment is to produce an insulating washer, and insert a metal spring contact inside. Contacts in double or triple internal tab washers can also be utilized in the present invention.

Figure 13:
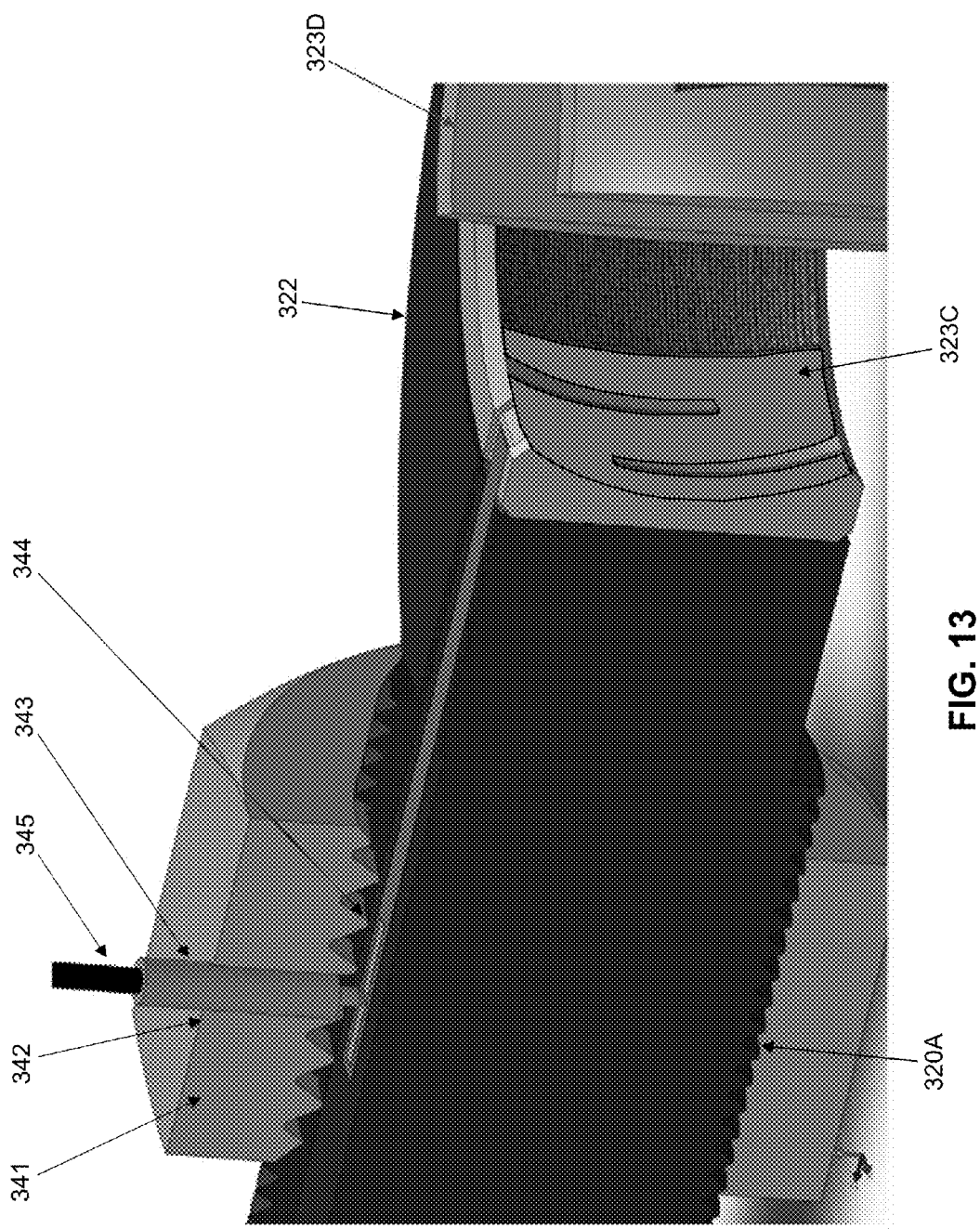
FIG. 13 is a schematic view showing a modified nut and insert with insulated lead.

Alternatively, and looking now at FIG. 13, the ball spring contact or other suitable contact may also be placed in the sidewall of a nut instead of a washer. More particularly, in this form of the invention, the nut 341 is drilled and optionally tapped radially, from the perimeter of the nut, preferably on a face, with a through-hole 342. An insert 343, comprising at least an insulating housing and a conductive core, is placed in the through-hole to connect the sensor electrode lead 344 and a wire 345 that protrudes from one end of the insert. The insert may be threaded like a set screw, and may have a hex or slot in the back end to assist installation. Alternatively, the insert 343 may be installed with adhesive only.

The embodiment of FIG. 13 requires that the contact point in the nut 341 be rotationally aligned with the sensor lead electrode 344 to make a connection. Another option is to utilize a washer or a nut with a keyway slot, and insert a separate key, which is equipped with an insulated electrical contact similar to that shown in FIG. 13.

FIGS. 11A-11D show a rod end with a 2-part construction. More typical is a rod end utilizing a 3-part construction, where a ball and race are inserted into a rod end housing, often called a banjo. In the Military Standard MS14101 and MS14103 bearings, the race has a feature on the outer edge, which is a groove, known as a staking groove, or "Grumman groove". MS14102 and MS14104 bearings have a chamfer at the corner of the race, to ease installation. The groove creates an area in the race where, upon application of sufficient force, the area deforms permanently to affix the race to the housing. The tools used to deform the race (e.g., via swaging) typically take the form of a clamp that compresses one or both sides of the race groove. The sensor leads could easily be severed by the tools used to install the bearings, such as tri-rollers. A modification to the tool, which may be utilized so as to not deform the area where the sensor lead exits the bearing, is one possible solution. Another possible solution is to ensure that the radial cut in the race traverses the staking groove well below the bottom of the staking groove, as is illustrated in FIGS. 14A and 14B. More particularly, a sensor lead 351 is routed away from a race inner edge 352 by cutting a first chamfered slot so as to reduce the angle the sensor must traverse, and by cutting a second radial channel 353 that is deeper than the staking groove by a sufficient thickness so as to enable the deformation of the staking groove by the installation tool, without touching the top of the sensor. Note that sensor lead 351 is secured to a sensor electrode 323C which is adjacent wear liner 323D.

An alternative process is illustrated in FIGS. 15A and 15B, where only the first cut is made at the race edge, and the sensor lead is left free and out of the way during the installation of the bearing to the part, such as a rod end, and then routed over top of the staking groove afterwards.

For the aforementioned MS14102 and MS14104 bearings, which have a chamfer on the outer edge, it is generally advantageous to provide a radial channel in the race, in which the sensor lead can be routed, so that the lead is not crushed by the forces necessary for installation. See FIGS. 16A and 16B. In FIG. 16A, a channel 361 is cut in the bearing race, connecting to a chamfer 362 that increases the radius of curvature for the sensor lead 363 to greater than 5× the sensor thickness. This modification allows the bearing to be inserted into a press-fit housing 364 (FIG. 16B).

Alternatively, a channel could be cut in the compression tool used to press the bearing into place so that the sensor lead is not damaged during installation.

Figure 17:
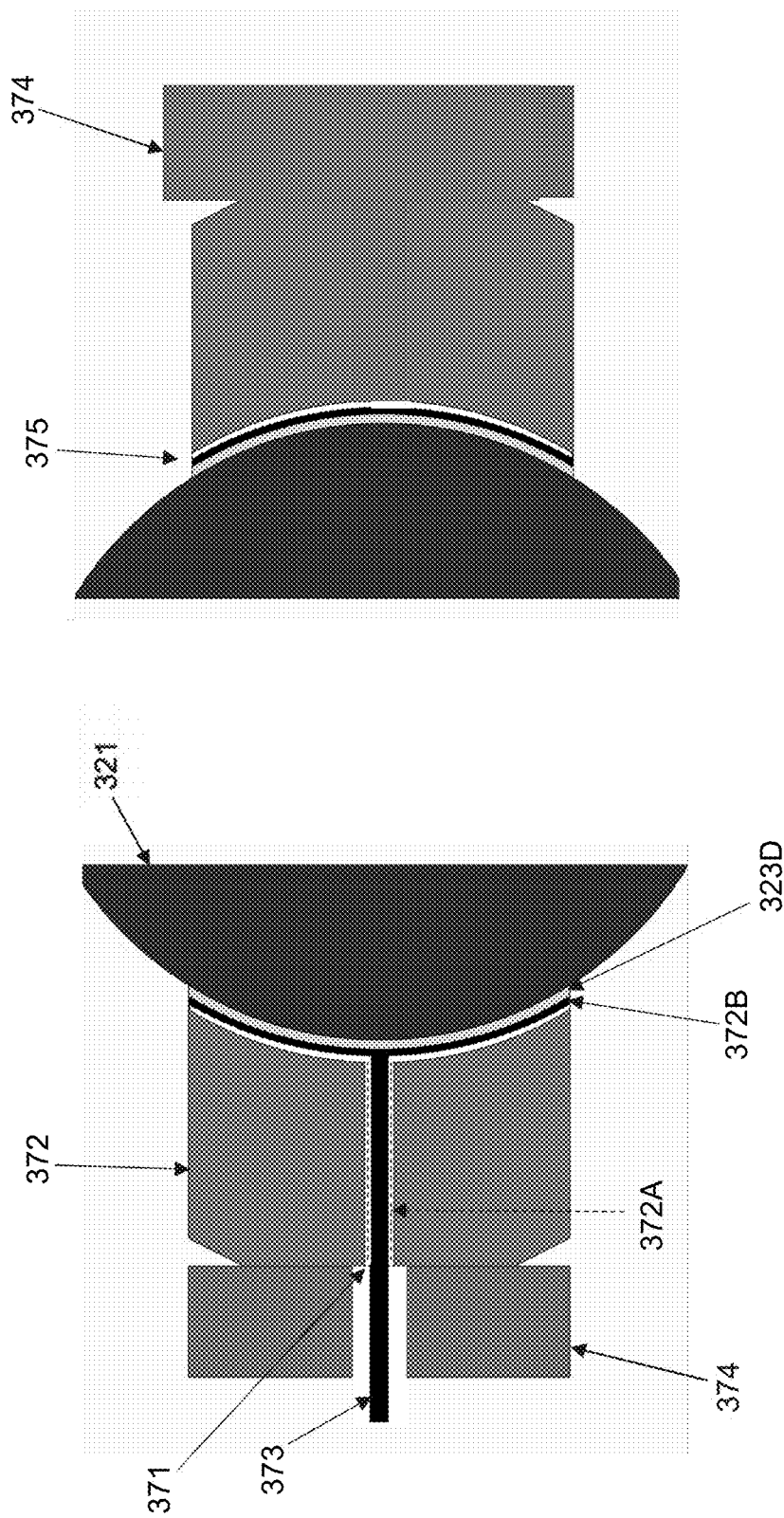
FIG. 17 is a schematic view showing how the sensor lead may be routed through the race of the bearing.

Looking next at FIG. 17, in another form of the invention, a hole 371 is drilled in the bearing race 372, through which a lead or spring contact 372A is inserted to touch the wear sensor electrode 372B. A corresponding contact and/or lead 373 is placed in the housing 374, such that when the bearing is inserted, electrical contact is made with the sensor 375. The contact 373 may be insulating with a conductive core, which may additionally be spring-loaded to contact the sensor lead. This construction has advantages in that the leads are protected from exposure, and both top and bottom faces of the bearing are left free of adornment. However, with this form of the invention, the bearing must be properly aligned rotationally with the contact in the housing.

The present invention includes a variety of novel aspects.

One novel aspect of the present invention is the modification of a spherical bearing to enable the installation of a sensor, comprising: creating a bevel at the edge of the race to ensure that the sensor lead sees a radius of curvature no less than 4 times the sensor thickness, and preferably 10 times the sensor thickness.

Another novel aspect of the present invention is the modification of a spherical bearing to enable the installation of a sensor, comprising: creating a channel in the race that is deeper than the staking groove, to enable installation of the bearing without damage to the sensor, and routing the sensor lead through the bottom of the channel.

Another novel aspect of the present invention is the modification of a spherical bearing to enable the installation of a sensor, comprising: creating a radial channel in the race that is deep enough to allow a compression tool to press on the face of the bearing without damage to the sensor, and routing the sensor lead through the bottom of the channel.

Another novel aspect of the present invention is the method of installing a sensor-equipped spherical bearing, by placing the sensor lead out of the path of the compression tool used to deform the metal surrounding a staking groove to fixate the race within a housing, and then affixing the sensor lead to the race and housing after the compression/swaging operation is complete.

Another novel aspect of the present invention is a method for making electrical contact to the wear sensor capable of surviving prolonged vibration, comprising: providing a substrate that is affixed to a component, the sensor leads passing underneath the substrate, metallized vias through the substrate that connect the traces in the sensor to electrical traces, and a connector on the top side of the substrate.

Another novel aspect of the present invention is a method for making electrical contact to a wear sensor in an assembly, the method comprising: providing a hole in the race; inserting an insulated electrical lead into the hole so that the one end of the lead contacts the wear sensor; and inserting the bearing into a housing having an insulated contact that touches the other end of the lead, thereby enabling the measurement of the capacitance between the wear sensor electrode and the ball, which is correlated to the thickness and condition of the insulating wear liner between the ball and race.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A spherical bearing comprising:
 a race;
 a ball;
 a wear lining; and
 a capacitive sensor positioned within or behind the wear lining to gauge wear of said wear lining;
 wherein a radial channel is cut along one face of said race, so as to enable the installation of a sensor lead to said capacitive sensor, wherein said radial channel in said race is deeper than a staking groove detent, in order to allow the installation of the spherical bearing without damage to said capacitive sensor and so as to allow routing of said sensor lead through a bottom of said radial channel.

2. A spherical bearing according to claim 1 wherein said race is beveled in an area along an edge where said race hugs said ball so as to ensure that said sensor a lead of said capacitive sensor sees a radius of curvature no less than 4 times the thickness of said capacitive sensor.

3. A spherical bearing according to claim 2 wherein said sensor lead of said capacitive sensor sees a radius of curvature of 10 times said capacitive sensor thickness.

4. A spherical bearing according to claim 1 wherein said capacitive sensor comprises an electrically conductive trace disposed between two layers of electrically insulating substrate material, and an electrical lead connected to said electrically conductive trace so as to enable an electrical connection to the capacitive sensor.

5. A spherical bearing according to claim 4 wherein the capacitive sensor further comprises tabs extending therefrom.

6. A spherical bearing according to claim 5 wherein the tabs comprise electrode pads for interrogation of the sensor.

7. A spherical bearing according to claim 6 wherein the tabs and electrode pads are connected to an antenna.

8. A spherical bearing according to claim 7 wherein the antenna is mounted on a face of the race.

9. A spherical bearing according to claim 4 wherein the capacitive sensor further comprises strain relief cuts enabling deformation of the sensor.

10. A spherical bearing according to claim 4 wherein the electrically insulating substrate material comprises a polyimide-based flexible substrate.

11. A spherical bearing according to claim 10 wherein the polyimide-based flexible substrate comprises at least one from the group consisting of urethanes, polyesters (PET), polyimides (PI), polyethylene napthalates (PEN), polyetherimides (PEI) and fuoropolymers (FEP).

* * * * *